(12) United States Patent
Inoue

(10) Patent No.: US 11,344,186 B2
(45) Date of Patent: May 31, 2022

(54) ENDOSCOPE OPTICAL SYSTEM AND ENDOSCOPE

(71) Applicant: FUJIFILM Corporation, Tokyo (JP)

(72) Inventor: Kazuki Inoue, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 326 days.

(21) Appl. No.: 16/386,271

(22) Filed: Apr. 17, 2019

(65) Prior Publication Data

US 2019/0320885 A1 Oct. 24, 2019

(30) Foreign Application Priority Data

Apr. 19, 2018 (JP) .............................. JP2018-080605

(51) Int. Cl.
  *G02B 27/14* (2006.01)
  *A61B 1/04* (2006.01)
  *A61B 1/00* (2006.01)
  *G02B 23/24* (2006.01)

(52) U.S. Cl.
  CPC ...... *A61B 1/00183* (2013.01); *A61B 1/00096* (2013.01); *A61B 1/04* (2013.01); *G02B 23/2423* (2013.01); *A61B 1/00009* (2013.01); *A61B 1/00179* (2013.01)

(58) Field of Classification Search
  CPC ... A61B 1/00183; A61B 1/00096; A61B 1/04; A61B 1/00179; A61B 1/00009; A61B 1/05; A61B 1/0005; A61B 1/00181; A61B 1/00188; G02B 23/2423; G02B 23/2446; G02B 23/243; G02B 23/04
  USPC .......................... 359/629; 600/109, 160–182
  See application file for complete search history.

(56) References Cited

U.S. PATENT DOCUMENTS

| 5,916,148 | A  | * | 6/1999  | Tsuyuki ............. A61B 1/00096 600/176 |
| 6,618,205 | B2 |   | 9/2003  | Murayama |
| 8,422,150 | B2 |   | 4/2013  | Takato |
| 8,896,940 | B2 |   | 11/2014 | Harada |
| 2012/0127567 | A1 | | 5/2012 | Schouwink et al. |

(Continued)

FOREIGN PATENT DOCUMENTS

| CN | 102422199 | 4/2012 |
| DE | 10221401  | 11/2002 |

(Continued)

OTHER PUBLICATIONS

"Office Action of Japan Counterpart Application", dated May 11, 2021, with English translation thereof, pp. 1-6.

(Continued)

*Primary Examiner* — Mahidere S Sahle
(74) *Attorney, Agent, or Firm* — JCIPRNET

(57) ABSTRACT

The endoscope optical system consists of: a first lens group that is used only for front viewing; a plurality of second lens groups that have a negative lens at a position closest to an object side and are used only for side viewing; a third lens group that is commonly used in front viewing and side viewing; and a synthesizing section that synthesizes the rays emitted from the first lens group and the rays emitted from the second lens groups and causes the synthesized rays to be incident into the third lens group. The rays emitted from the first lens group and the rays emitted from the second lens groups are imaged on a same plane.

15 Claims, 10 Drawing Sheets

EXAMPLE 1

(56) References Cited

U.S. PATENT DOCUMENTS

2016/0015258 A1\* 1/2016 Levin .................. A61B 1/0005
                                                    600/109
2016/0088204 A1    3/2016 Liang et al.
2017/0351086 A1   12/2017 Takahashi

FOREIGN PATENT DOCUMENTS

| JP | H07311348 | 11/1995 | | |
|---|---|---|---|---|
| JP | 2005261557 | 9/2005 | | |
| JP | 2008-309860 | 12/2008 | | |
| JP | 2008309860 A | \* 12/2008 | ............. | A61B 1/041 |
| JP | 2009000506 | 1/2009 | | |
| JP | 2011117665 | 6/2011 | | |
| JP | 2016-521607 | 7/2016 | | |
| JP | 6000823 | 10/2016 | | |
| WO | 2008111970 | 9/2008 | | |
| WO | 2012008312 | 1/2012 | | |
| WO | 2013065294 | 5/2013 | | |
| WO | 2017110351 | 6/2017 | | |

OTHER PUBLICATIONS

Office Action of China Counterpart Application, with English translation thereof, dated Jan. 28, 2022, pp. 1-12.

\* cited by examiner

EXAMPLE 1

EXAMPLE 1

FRONT VIEW + SIDE VIEW

FRONT VIEW

SIDE VIEW

EXAMPLE 2

EXAMPLE 2

FRONT VIEW + SIDE VIEW

FRONT VIEW

SIDE VIEW

EXAMPLE 1

EXAMPLE 2

ENDOSCOPE OPTICAL SYSTEM AND ENDOSCOPE

CROSS REFERENCE TO RELATED APPLICATIONS

The present application claims priority under 35 U.S.C. § 119 to Japanese Patent Application No. 2018-080605 filed on Apr. 19, 2018. The above application is hereby expressly incorporated by reference, in its entirety, into the present application.

BACKGROUND OF THE INVENTION

1. Field of the Invention

The present invention relates to an endoscope optical system and an endoscope having the endoscope optical system.

2. Description of the Related Art

In the related art, insertion type endoscopes, in which an image of a body cavity is captured by inserting an elongated insertion section having an imaging device built in a distal end portion thereof from a mouth, a nose, or the like of a subject, have been popularized in the medical field. In recent years, endoscopes capable of both front viewing and side viewing have been proposed. For example, endoscope optical systems used for an endoscope capable of both front viewing and side viewing in Patent JP2016-521607A, JP6000823B, JP2008-309860A, and WO17/110351 are known.

SUMMARY OF THE INVENTION

In the endoscope optical systems described in JP2016-521607A, JP6000823B, and JP2008-309860A, an image of the side view region is formed around an image of a front view region. Thus, there is a problem that it is difficult to visually recognize the image of the side view region.

The endoscope optical system described in WO17/110351 is able to separately acquire two kinds of images of a front view region and a side view region. Thus, an image with high visibility can be acquired. However, the endoscope optical system described in WO17/110351 separately acquires the two kinds of images of the front view region and the side view region are by switching the optical path for front viewing and the optical path for side viewing. Thus, there is a problem that it is not possible to simultaneously perform both front viewing and side viewing and observation efficiency is poor.

The present invention has been made in consideration of the above-mentioned situations. It is an object of the present invention to provide an endoscope optical system, which is capable of separately and simultaneously acquiring two kinds of images of a front view region and a side view region, and an endoscope having the endoscope optical system.

An endoscope optical system of the present invention is capable of both front viewing and side viewing. The endoscope optical system consists of: a first lens group that is used only for front viewing; a plurality of second lens groups that have a negative lens at a position closest to an object side and are used only for side viewing; a third lens group that is commonly used in front viewing and side viewing; and a synthesizing section that has at least one planar synthesis surface, which transmits rays emitted from the first lens group and reflects rays emitted from the second lens groups, so as to synthesize the rays emitted from the first lens group and the rays emitted from the second lens groups and cause the synthesized rays to be incident into the third lens group. The rays emitted from the first lens group and the rays emitted from the second lens groups are imaged on a same plane.

In the endoscope optical system of the present invention, it is preferable that the second lens group has two or more negative lenses continuously from a position closest to the object side.

In addition, it is preferable that an entire surface on which the synthesis surface is formed is a partially transmissive and partially reflective surface.

In addition, it is preferable that the third lens group has a third-a cemented lens, in which a positive lens and a negative lens are cemented in order from the object side, at a position closest to an image side.

It is preferable that the first lens group has a first-a cemented lens in which a positive lens and a negative lens are cemented in order from the object side.

Further, assuming that a focal length of the second lens groups is f2, and a composite focal length of the second lens groups and the third lens group is F2, it is preferable to satisfy Conditional Expression (1). It is more preferable to satisfy Conditional Expression (1-1).

$$-0.95 < f2/F2 < -0.1 \quad (1)$$

$$-0.9 < f2/F2 < -0.15 \quad (1\text{-}1)$$

In addition, it is preferable that assuming that a focal length of the first lens group is f1, and a composite focal length of the first lens group and the third lens group is F1, it is preferable to satisfy Conditional Expression (2). It is more preferable to satisfy Conditional Expression (2-1).

$$-1.5 < f1/F1 < -1.1 \quad (2)$$

$$-1.45 < f1/F1 < -1.15 \quad (2\text{-}1)$$

Further, assuming that a focal length of the third lens group is f3, and a composite focal length of the first lens group and the third lens group is F1, it is preferable to satisfy Conditional Expression (3). It is more preferable to satisfy Conditional Expression (3-1).

$$5 < f3/F1 < 12 \quad (3)$$

$$7 < f3/F1 < 10 \quad (3\text{-}1)$$

In the case where the third-a cemented lens is provided in the third lens group, assuming that an Abbe number of the positive lens of the third-a cemented lens is $vd31$, and an Abbe number of the negative lens of the third-a cemented lens is $vd32$, it is preferable to satisfy Conditional Expression (4). It is more preferable to satisfy Conditional Expression (4-1).

$$38 < vd31 - vd32 < 58 \quad (4)$$

$$40 < vd31 - vd32 < 56 \quad (4\text{-}1)$$

In the case where the third-a cemented lens is provided in the third lens group, assuming that a refractive index of the positive lens of the third-a cemented lens is $n31$, and a refractive index of the negative lens of the third-a cemented lens is $n32$, it is preferable to satisfy Conditional Expression (5). It is more preferable to satisfy Conditional Expression (5-1).

$$-0.45 < n31 - n32 < -0.28 \quad (5)$$

$$-0.43 < n31 - n32 < -0.3 \quad (5\text{-}1)$$

In the case where the first-a cemented lens is provided in the first lens group, assuming that an Abbe number of the positive lens of the first-a cemented lens is vd11, and an Abbe number of the negative lens of the first-a cemented lens is vd12, it is preferable to satisfy Conditional Expression (6). It is more preferable to satisfy Conditional Expression (6-1).

$$-40<vd11-vd12<-10 \quad (6)$$

$$-38<vd11-vd12<-12 \quad (6\text{-}1)$$

Further, it is preferable that the synthesis surface is inclined with respect to an axis perpendicular to an optical axis of the third lens group.

An endoscope of the present invention comprises the endoscope optical system of the present invention described above.

The endoscope optical system of the present invention is capable of both front viewing and side viewing. The endoscope optical system comprises: a first lens group that is used only for front viewing; a plurality of second lens groups that have a negative lens at a position closest to an object side and are used only for side viewing; a third lens group that is commonly used in front viewing and side viewing; and a synthesizing section that has at least one planar synthesis surface, which transmits rays emitted from the first lens group and reflects rays emitted from the second lens groups, so as to synthesize the rays emitted from the first lens group and the rays emitted from the second lens groups and cause the synthesized rays to be incident into the third lens group. The rays emitted from the first lens group and the rays emitted from the second lens groups are imaged on a same plane. Therefore, it is possible to provide an endoscope optical system, which is capable of separately and simultaneously acquiring two kinds of images of a front view region and a side view region, and an endoscope having the endoscope optical system.

DESCRIPTION OF THE PREFERRED EMBODIMENTS

Figure 1:
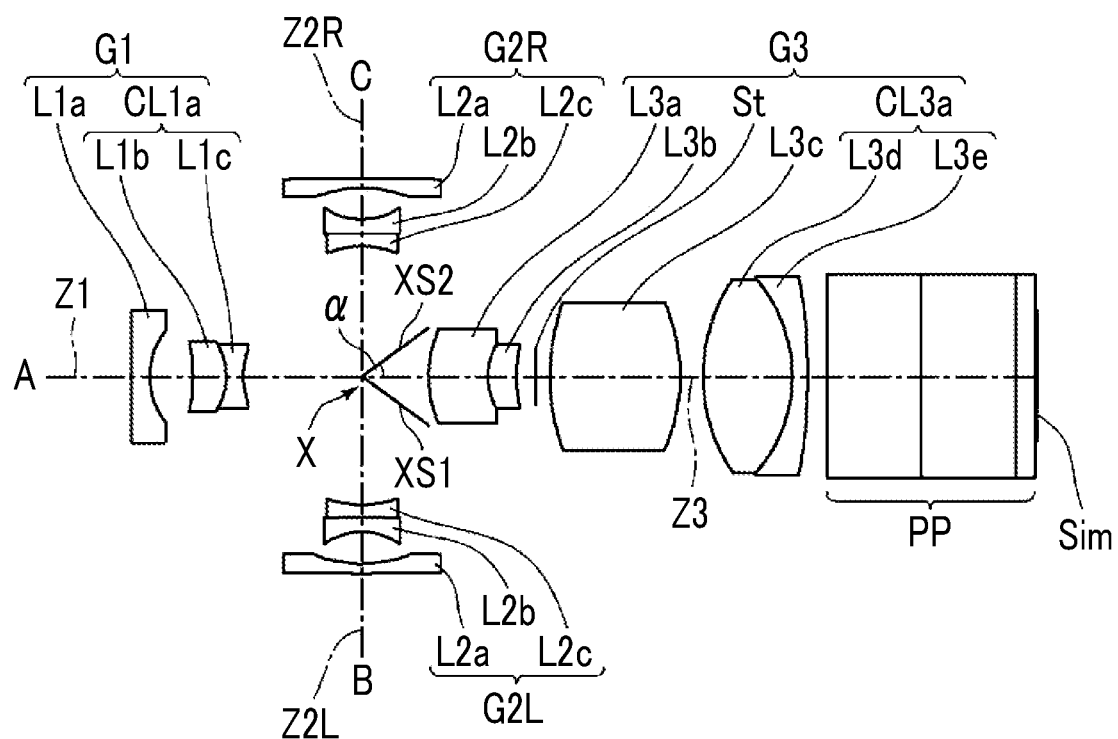
FIG. 1 is a cross-sectional view illustrating a configuration of an endoscope optical system (common to Example 1) according to an embodiment of the present invention.
Figure 2:
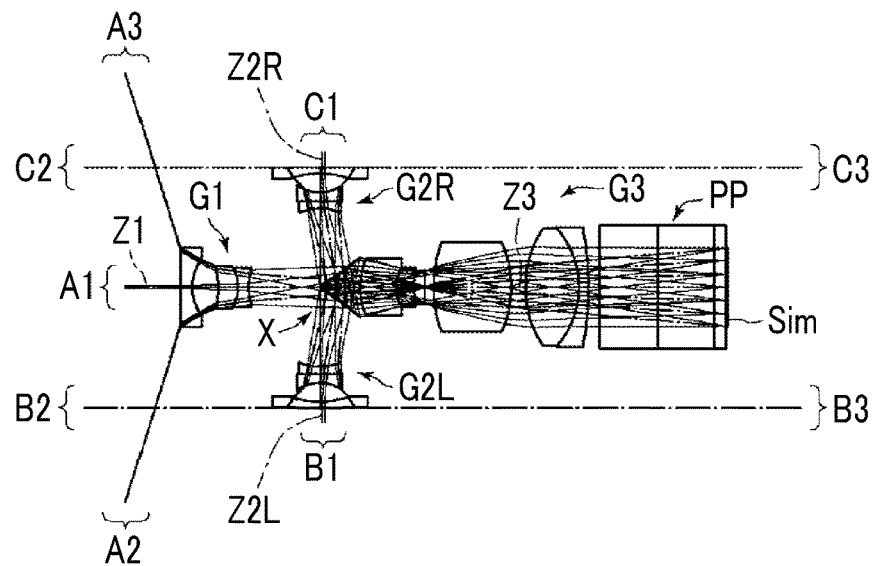
FIG. 2 is an optical path diagram of the endoscope optical system of Example 1.
Figure 2:
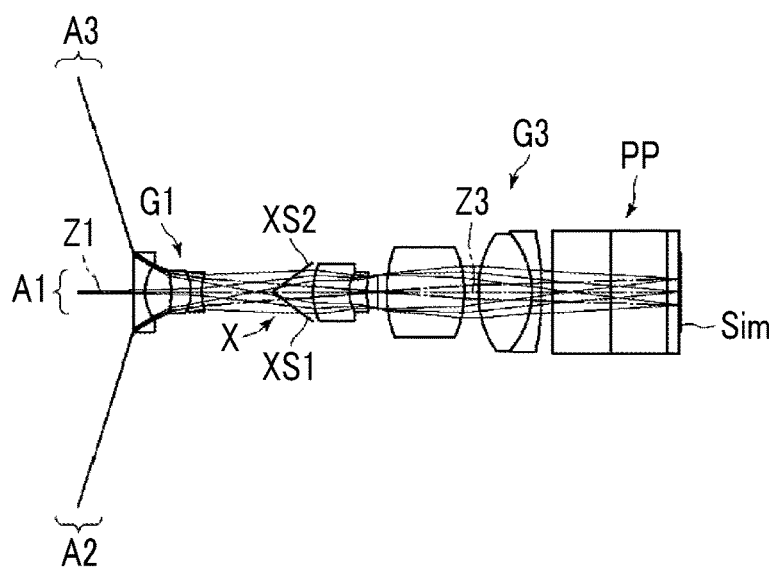
Figure 2:
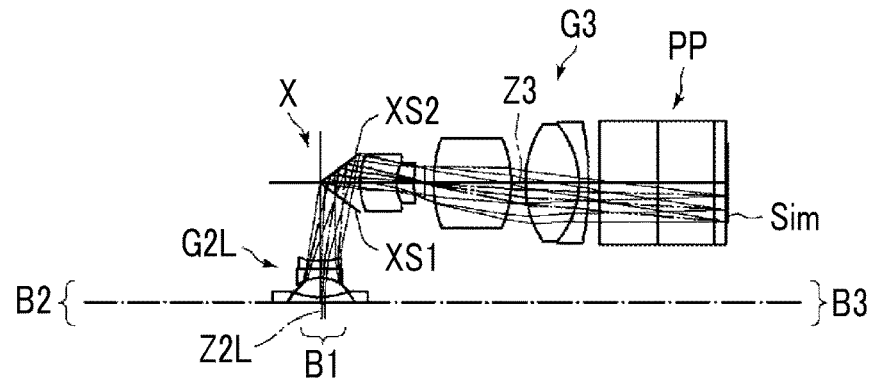
Figure 3:
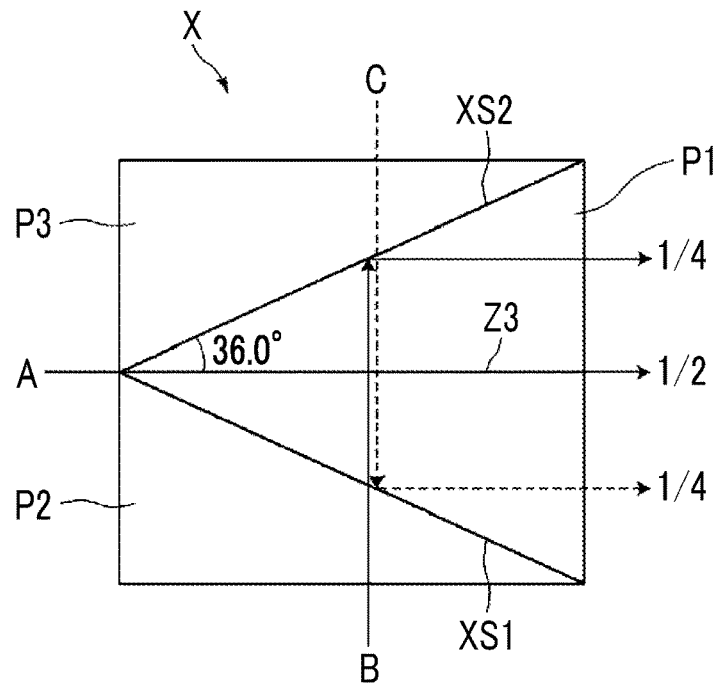
FIG. 3 is a schematic configuration diagram of a synthesizing section of the endoscope optical system of Example 1.

Hereinafter, an embodiment of the present invention will be described in detail with reference to the drawings. FIG. 1 is a cross-sectional view illustrating a configuration of an endoscope optical system according to an embodiment of the present invention. FIG. 2 is an optical path diagram of the endoscope optical system. FIG. 3 is a schematic configuration diagram of a synthesizing section of the endoscope optical system. The exemplary configuration shown in FIGS. 1 and 2 is the same as a configuration of the endoscope optical system of Example 1 to be described later. In each of FIGS. 1 and 2, in a case where the optical path is developed, the left side is an object side, and the right side is an image side. In addition, an aperture stop St shown in the drawing does not necessarily show its real size and shape, but show a position on an optical axis Z. Further, in FIG. 2, the upper part shows optical paths for both front and side views (on-axis rays A1 in the front view, the rays A2 and A3 with the maximum angle of view, on-axis rays B1 in the left side view and the rays B2 and B3 with the maximum angle of view, on-axis rays C1 in the right side view, and rays C2 and C3 with the maximum angle of view). The middle part shows an optical path only for the front view (on-axis rays A1 in the front view and rays A2 and A3 with the maximum angle of view). The lower part shows an optical path only for the left side view (on-axis rays B1 in the left side view and rays B2 and B3 with the maximum angle of view).

Further, FIGS. 1 and 2 show an example in which an optical member PP having an incident surface and an exit surface parallel to each other is disposed between the endoscope optical system and the imaging surface Sim. It is assumed that the optical member PP is an optical path changing prism, a filter, a cover glass, and the like for deflecting the optical path. In the present invention, it may be possible to adopt a configuration in which the optical member PP is omitted.

The endoscope optical system according to the present embodiment is an endoscope optical system that is capable of both front viewing and side viewing. The endoscope optical system includes: a first lens group G1 that is used only for front viewing; second lens groups G2L and G2R that have a negative lens at a position closest to the object side and are used only for side viewing; a third lens group G3 that is commonly used in front viewing and side viewing; and a synthesizing section X that has planar synthesis surfaces XS1 and XS2, which transmit rays emitted from the first lens group G1 and reflect rays emitted from the second lens groups G2L and G2R, so as to synthesize the rays emitted from the first lens group G1 and the rays emitted from the second lens groups G2L and G2R and cause the synthesized rays to be incident into the third lens group G3. The rays emitted from the first lens group G1 and the rays emitted from the second lens groups G2L and G2R are imaged on a same plane. In the endoscope optical system of the present embodiment, the two second lens groups G2L and G2R have exactly the same lens configuration, but a plurality of second lens groups may have different lens configurations.

As shown in FIG. 3, in the synthesizing section X, three prisms P1, P2, and P3 are cemented, a synthesis surface XS1 is formed at the boundary surface between the prisms P1 and P2, and a synthesis surface XS2 is formed at the boundary surface between the prisms P1 and P3. The synthesis surfaces XS1 and XS2 are half mirror surfaces which are partially transmissive and partially reflective surfaces. The synthesis surfaces XS1 and XS2 are configured to be inclined by 36.0° with respect to the optical axis Z3 of the third lens group G3.

Here, it is preferable that an entire surface, on which the synthesis surface XS1 or the synthesis surface XS2 is formed, is a partially transmissive and partially reflective surface. As described above, instead of forming a partially transmissive and partially reflective surface on a part of one surface, by forming a partially transmissive and partially reflective surface on the entire one surface, it is possible to easily manufacture the synthesizing section X.

The rays emitted from the first lens group G1 (the rays in the direction A in FIG. 3) pass through the synthesizing section X and are transmitted to the side of the third lens group G3. However, at this time, the rays emitted from the first lens group G1 pass through the synthesis surface XS1 or the synthesis surface XS2 once, and thus the light amount decreases to ½. Further, the rays emitted from the second lens group G2L (the rays in the direction B in FIG. 3) are deflected toward the third lens group G3 by the synthesizing section X. However, at this time, the rays emitted from the second lens group G2L are transmitted through the synthesis surface XS1 and are thereafter reflected by the synthesis surface XS2, and thus the light amount decreases to ¼.

Likewise, the rays emitted from the second lens group G2R (the rays in the direction C in FIG. 3) are also deflected toward the third lens group G3 by the synthesizing section X. However, at this time, the rays emitted from the second lens group G2R are transmitted through the synthesis surface XS2 and are thereafter reflected by the synthesis surface XS1, and thus the light amount decreases to ¼. Regarding the decrease in light amount caused by passing through the synthesizing section X as described above, the influence of the decrease can be reduced by correcting the image signal acquired by the imaging element in a case where the endoscope optical system is incorporated in the endoscope.

The angles of inclination of the synthesis surfaces XS1 and XS2 with respect to the optical axis Z3 of the third lens group G3 are not particularly limited. However, it is preferable that the synthesis surfaces XS1 and XS2 are inclined with respect to the axis perpendicular to the optical axis Z3 of the third lens group G3 (the synthesis surfaces XS1 and XS2 are not inclined by 90° with respect to the optical axis Z3 of the third lens group G3). With such a configuration, the image height of the side view region can be adjusted.

The partially transmissive and partially reflective surfaces of the synthesis surfaces XS1 and XS2 are not limited to the half mirror surface having the same transmittance and reflectance but may be surfaces having different transmittances and reflectances.

Further, the number of synthesis surfaces of the synthesizing section is not limited to two, and may be one or three or more.

As described above, the endoscope optical system according to the present embodiment, the optical system necessary for front viewing and the optical system necessary for side viewing share some lens groups (the third lens group G3). Thereby, it is possible to reduce the size and cost of the entire endoscope optical system.

Further, in each of the second lens groups G2L and G2R used only for side viewing, by providing a negative lens at a position closest to the object side, it is possible to achieve wide angle in the side view region.

Further, by providing the synthesizing section X, the rays emitted from the first lens group G1 for front viewing and the rays emitted from the second lens groups G2L and G2R for side viewing are synthesized, and both rays for front viewing and side viewing are imaged on the same plane. With such a configuration, it is sufficient to use only one imaging element in a case where the endoscope optical system is incorporated in the endoscope. As a result, it is possible to reduce the size and cost of the entire endoscope including the endoscope optical system. In addition, it is possible to simultaneously perform observation in a plurality of directions including the front view direction and the side view direction.

Further, instead of forming an image of the side view region around the image of the front view region, the two kinds of images of the front view region and the side view region are separately and simultaneously acquired. Therefore, it is possible to make the side view region widely seen, and it is possible to further improve the observation efficiency.

In the endoscope optical system of the present embodiment, it is preferable that the second lens groups G2L and G2R have two or more negative lenses continuously from a position closest to the object side. With such a configuration, the negative refractive power necessary for widening the angle of the second lens groups G2L and G2R can be shared by a plurality of negative lenses. As a result, occurrence of various aberrations can be suppressed.

In addition, it is preferable that the third lens group G3 has a third-a cemented lens, in which a positive lens and a negative lens are cemented in order from the object side, at a position closest to the image side. With such a configuration, there is an advantage in suppressing lateral chromatic aberration and longitudinal chromatic aberration.

Further, it is preferable that the first lens group G1 has a first-a cemented lens in which a positive lens and a negative lens are cemented in order from the object side. With such a configuration, there is an advantage in suppressing lateral chromatic aberration.

Further, assuming that a focal length of the second lens groups G2L and G2R is f2 and a composite focal length of the second lens groups G2L and G2R and the third lens group G3 is F2, it is preferable to satisfy Conditional Expression (1). By not allowing the result of the conditional expression (1) to be equal to or less than the lower limit, it is possible to suppress field curvature. By not allowing the result of Conditional Expression (1) to be equal to or greater than the upper limit, it is possible to maintain the angle of view while suppressing the diameter of the lens. In addition, in a case where Conditional Expression (1-1) is satisfied, it is possible to obtain more favorable characteristics.

$$-0.95 < f2/F2 < -0.1 \tag{1}$$

$$-0.9 < f2/F2 < -0.15 \tag{1-1}$$

Further, assuming that a focal length of the first lens group G1 is f1, and a composite focal length of the first lens group G1 and the third lens group G3 is F1, it is preferable to satisfy Conditional Expression (2). By not allowing the result of the conditional expression (2) to be equal to or less than the lower limit, it is possible to suppress field curvature.

By not allowing the result of Conditional Expression (2) to be equal to or greater than the upper limit, it is possible to maintain the angle of view while suppressing the diameter of the lens. In addition, in a case where Conditional Expression (2-1) is satisfied, it is possible to obtain more favorable characteristics.

$$-1.5 < f1/F1 < -1.1 \qquad (2)$$

$$-1.45 < f1/F1 < -1.15 \qquad (2-1)$$

Further, assuming that a focal length of the third lens group G3 is f3 and a composite focal length of the first lens group G1 and the third lens group G3 is F1, it is preferable to satisfy Conditional Expression (3). By not allowing the result of Conditional Expression (3) to be equal to or less than the lower limit, it is possible to minimize the angle of incidence on the imaging element in a case where the endoscope optical system is incorporated in the endoscope. By not allowing the result of the conditional expression (3) to be equal to or greater than the upper limit, it is possible to suppress field curvature. In addition, in a case where Conditional Expression (3-1) is satisfied, it is possible to obtain more favorable characteristics.

$$5 < f3/F1 < 12 \qquad (3)$$

$$7 < f3/F1 < 10 \qquad (3-1)$$

In the case where the third-a cemented lens is provided in the third lens group G3, assuming that an Abbe number of the positive lens of the third-a cemented lens is vd31 and an Abbe number of the negative lens of the third-a cemented lens is vd32, it is preferable to satisfy Conditional Expression (4). By not allowing the result of Conditional Expression (4) to be equal to or less than the lower limit, it is possible to suppress lateral chromatic aberration. By not allowing the result of Conditional Expression (4) to be equal to or greater than the upper limit, it is possible to suppress longitudinal chromatic aberration. In a case where Conditional Expression (4-1) is satisfied, it is possible to obtain more favorable characteristics.

$$38 < vd31 - vd32 < 58 \qquad (4)$$

$$40 < vd31 - vd32 < 56 \qquad (4-1)$$

Further, in the case where the third-a cemented lens is provided in the third lens group G3, assuming that a refractive index of the positive lens of the third-a cemented lens is n31 and a refractive index of the negative lens of the third-a cemented lens is n32, it is preferable to satisfy Conditional Expression (5). By not allowing the result of Conditional Expression (5) to be equal to or less than the lower limit, it is possible to suppress spherical aberration. By not allowing the result of the conditional expression (5) to be equal to or greater than the upper limit, it is possible to suppress field curvature. In addition, in a case where Conditional Expression (5-1) is satisfied, it is possible to obtain more favorable characteristics.

$$-0.45 < n31 - n32 < -0.28 \qquad (5)$$

$$-0.43 < n31 - n32 < -0.3 \qquad (5-1)$$

In the case where the first-a cemented lens is provided in the first lens group G1, assuming that an Abbe number of the positive lens of the first-a cemented lens is vd11 and an Abbe number of the negative lens of the first-a cemented lens is vd12, it is preferable to satisfy Conditional Expression (6). By satisfying Conditional Expression (6), it is possible to suppress lateral chromatic aberration. In addition, in a case where Conditional Expression (6-1) is satisfied, it is possible to obtain more favorable characteristics.

$$-40 < vd11 - vd12 < -10 \qquad (6)$$

$$-38 < vd11 - vd12 < -12 \qquad (6-1)$$

Next, numerical examples of the endoscope optical system of the present invention will be described. First, the endoscope optical system of Example 1 will be described. FIG. 1 is a cross-cross-sectional view illustrating the configuration of the endoscope optical system of Example 1. FIG. 2 is an optical path diagram of the endoscope optical system of Example 1. In FIGS. 1 and 2 and FIGS. 4 and 5 corresponding to Example 2 to be described later, in a case where the optical path is developed, the left side is the object side and the right side is the image side. In addition, the aperture stop St shown in the drawings does not necessarily indicate its size or shape, and indicates a position thereof on the optical axis Z. Further, in FIG. 2 and FIG. 5 corresponding to Example 2 to be described later, the upper part shows optical paths for both front and side views (on-axis rays A1 in the front view, the rays A2 and A3 with the maximum angle of view, on-axis rays B1 in the left side view and the rays B2 and B3 with the maximum angle of view, on-axis rays C1 in the right side view, and rays C2 and C3 with the maximum angle of view). The middle part shows an optical path only for the front view (on-axis rays A1 in the front view and rays A2 and A3 with the maximum angle of view). The lower part shows an optical path only for the left side view (on-axis rays B1 in the left side view and rays B2 and B3 with the maximum angle of view).

The endoscope optical system of Example 1 is composed of a first lens group G1, second lens groups G2L and G2R, a third lens group G3, and a synthesizing section X. The first lens group G1 is used only for front viewing. The second lens groups G2L and G2R are used only for side viewing. The third lens group G3 is commonly used in front viewing and side viewing. The synthesizing section X has planar synthesis surfaces XS1 and XS2 that transmit the rays emitted from the first lens group G1 and reflect the rays emitted from the second lens groups G2L and G2R so as to synthesize the rays emitted from the first lens group G1 and the rays emitted from the second lens groups G2L and G2R through the synthesis surfaces XS1 and XS2 and cause the synthesized rays to be incident into the third lens group G3.

The first lens group G1 is composed of three lenses L1a to L1c. The positive lens L1b and the negative lens L1c are cemented to form a first-a cemented lens CL1a.

The second lens groups G2L and G2R have the same lens configuration, and each of those is composed of three lenses L2a to L2c.

The third lens group G3 is composed of an aperture stop St and five lenses L3a to L3e. The positive lens L3d and the negative lens L3e are cemented to form the third-a cemented lens CL3a.

The synthesis surfaces XS1 and XS2 of the synthesizing section X are half mirror surfaces.

Table 1 shows basic lens data of the front view optical path of the endoscope optical system of Example 1. Table 2 shows data about specifications of the front view optical path. Table 3 shows basic lens data of the side view optical path. Table 4 shows data about specifications of the side view optical path. Hereinafter, meanings of the reference signs in the tables are, for example, as described in Example 1, and are basically the same as those in Example 2.

In the lens data of Tables 1 and 3, the column of the surface number shows surface numbers. The surface of the elements closest to the magnification side is the first surface, and the surface numbers sequentially increase toward the reduction side. The column of the radius of curvature shows radii of curvature of the respective surfaces. The column of the on-axis surface distance shows distances on the optical axis Z between the respective surfaces and the subsequent surfaces. Further, the column of n shows a refractive index of each optical element at the d line (a wavelength of 587.6 nm (nanometers)), and the column of ν shows an Abbe number of each optical element at the d line (a wavelength of 587.6 nm (nanometers)). Furthermore, the sign of the radius of curvature is positive in a case where a surface has a shape convex toward the magnification side, and is negative in a case where a surface has a shape convex toward the reduction side. The basic lens data additionally shows data about the half mirror surface, the aperture stop St, and the optical member PP. In a place of a surface number of a surface corresponding to the half mirror surface, the surface number and a term of "half mirror" are noted. Further, in a place of a surface number of a surface corresponding to the aperture stop St, the surface number and a term of "stop" are noted.

In the data about the specifications of Tables 2 and 4, values of the focal length f, the F number FNo., and the total angle of view 2ω(°) are noted.

In the basic lens data and data about specification, "°" is used as a unit of angle, and "mm" (millimeter) is used as a unit of length, but appropriate different units may be used since the optical system can be used even in a case where the system is enlarged or reduced in proportion.

TABLE 1

Example 1 (First Lens Group + Third Lens Group)
Lens Data (n, ν are based on the d line)

| Surface Number | Radius of Curvature | Surface Distance | n | ν |
|---|---|---|---|---|
| 1 | ∞ | 0.3000 | 1.88300 | 40.81 |
| 2 | 1.1542 | 0.6903 | | |
| 3 | −2.8288 | 0.5312 | 1.94948 | 17.85 |
| 4 | −1.0000 | 0.2722 | 1.84844 | 38.10 |
| 5 | 1.3568 | 2.9464 | | |
| 12 | 1.8654 | 0.9405 | 1.94522 | 30.25 |
| 13 | 1.0070 | 0.4624 | 1.50235 | 55.54 |
| 14 | 3.0001 | 0.2957 | | |
| 15(Stop) | ∞ | 0.2280 | | |
| 16 | 3.4342 | 2.0554 | 1.59868 | 61.95 |
| 17 | −2.8358 | 0.3610 | | |
| 18 | 2.6892 | 1.4205 | 1.50577 | 79.10 |
| 19 | −2.2913 | 0.2500 | 1.86263 | 27.55 |
| 20 | −8.4552 | 0.3000 | | |
| 21 | ∞ | 1.5000 | 1.55920 | 53.92 |
| 22 | ∞ | 1.5000 | 1.55920 | 53.92 |
| 23 | ∞ | 0.3000 | 1.51633 | 64.05 |
| 24 | ∞ | | | |

TABLE 2

Example 1 (First Lens Group + Third Lens Group) Specification (d line)

| | |
|---|---|
| f | 0.35 |
| FNo. | 3.71 |
| 2ω[°] | 144.8 |

TABLE 3

Example 1 (Second Lens Group + Third Lens Group)
Lens Data (n, ν are based on the d line)

| Surface Number | Radius of Curvature | Surface Distance | n | ν |
|---|---|---|---|---|
| 6 | 118.6844 | 0.1500 | 1.88300 | 40.81 |
| 7 | 2.0936 | 0.5007 | | |
| 8 | −1.0585 | 0.2258 | 1.52485 | 64.04 |
| 9 | −264.5611 | 0.1997 | 1.88551 | 39.45 |
| 10 | 1.5605 | 2.0354 | | |
| 11(Half Mirror) | ∞ | 1.0612 | | |
| 12 | 1.8654 | 0.9405 | 1.94522 | 30.25 |
| 13 | 1.0070 | 0.4624 | 1.50235 | 55.54 |
| 14 | 3.0001 | 0.2957 | | |
| 15(Stop) | ∞ | 0.2280 | | |
| 16 | 3.4342 | 2.0554 | 1.59868 | 61.95 |
| 17 | −2.8358 | 0.3610 | | |
| 18 | 2.6892 | 1.4205 | 1.50577 | 79.10 |
| 19 | −2.2913 | 0.2500 | 1.86263 | 27.55 |
| 20 | −8.4552 | 0.3000 | | |
| 21 | ∞ | 1.5000 | 1.55920 | 53.92 |
| 22 | ∞ | 1.5000 | 1.55920 | 53.92 |
| 23 | ∞ | 0.3000 | 1.51633 | 64.05 |
| 24 | ∞ | | | |

TABLE 4

Example 1 (Second Lens Group + Third Lens Group) Specification (d line)

| | |
|---|---|
| f | 0.88 |
| FNo. | 3.69 |
| 2ω[°] | 180.0 |

Figure 6:
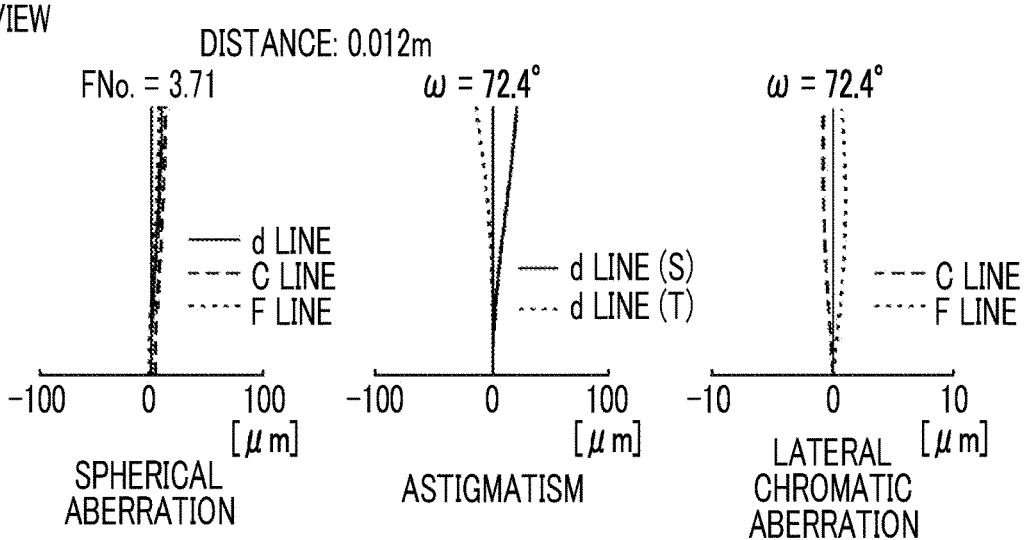
FIG. 6 is a diagram illustrating aberrations of the endoscope optical system of Example 1 of the present invention.
Figure 6:
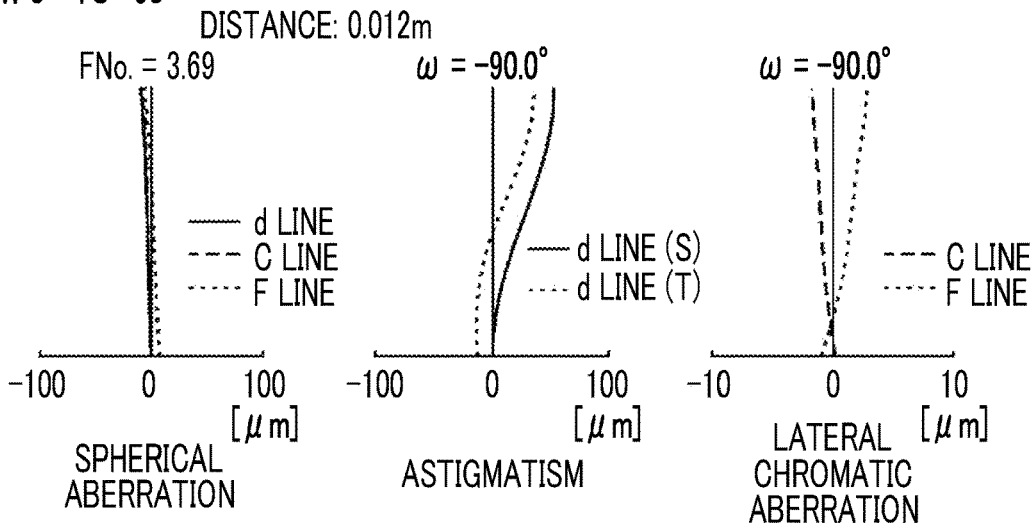
Figure 6:
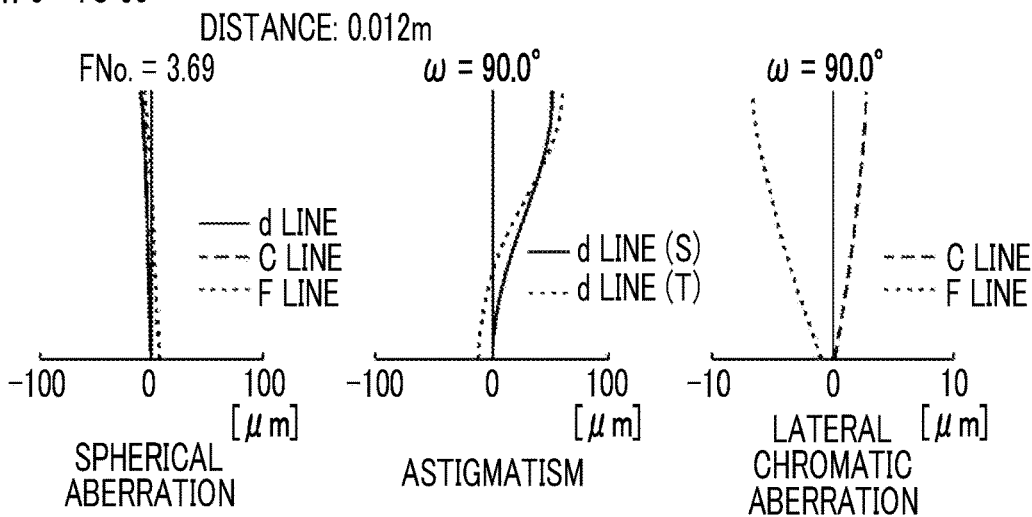

FIG. 6 shows a diagram of aberrations of the endoscope optical system of Example 1. Spherical aberration, astigmatism, and lateral chromatic aberration in the front view optical path are shown in order from the upper left side in FIG. 6. Spherical aberration, astigmatism, and lateral chromatic aberration at a position closer to the image side than the optical axis Z2L/Z2R of the second lens group G2L/G2R in the side view optical path are shown in order from the middle left side. Spherical aberration, astigmatism, and lateral chromatic aberration at a position closer to the object side than the optical axis Z2L/Z2R of the second lens group G2L/G2R in the side view optical path are shown in order from the lower left side.

Each aberration diagram illustrating spherical aberration and astigmatism shows aberration at the d line (a wavelength of 587.6 nm (nanometers)) which is set as a reference wavelength. In the spherical aberration diagram, aberrations at the d line (a wavelength of 587.6 nm (nanometers)), the C line (a wavelength of 656.3 nm (nanometers)), and the F line (a wavelength of 486.1 nm (nanometers)) are respectively indicated by the solid line, the long dashed line, and the short dashed line. In the astigmatism diagram, aberrations in sagittal and tangential directions are respectively indicated by the solid line and the short dashed line. In the lateral chromatic aberration diagram, aberrations at the C line (a wavelength of 656.3 nm (nanometers)) and F line (a wavelength of 486.1 nm (nanometers)) are respectively indicated by the long dashed line and the short dashed line. In addition, in the spherical aberration diagram, FNo. means an F number. In the other aberration diagrams, w means a half angle of view.

Figure 4:
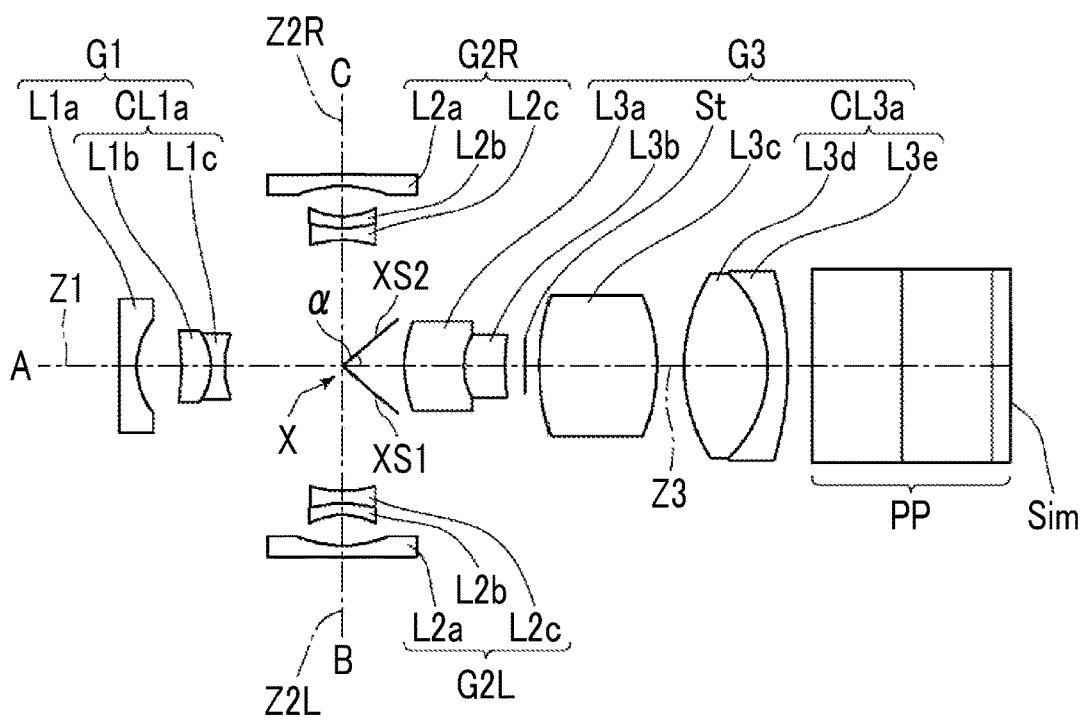
FIG. 4 is a cross-sectional view illustrating a configuration of an endoscope optical system of Example 2 of the present invention.
Figure 5:
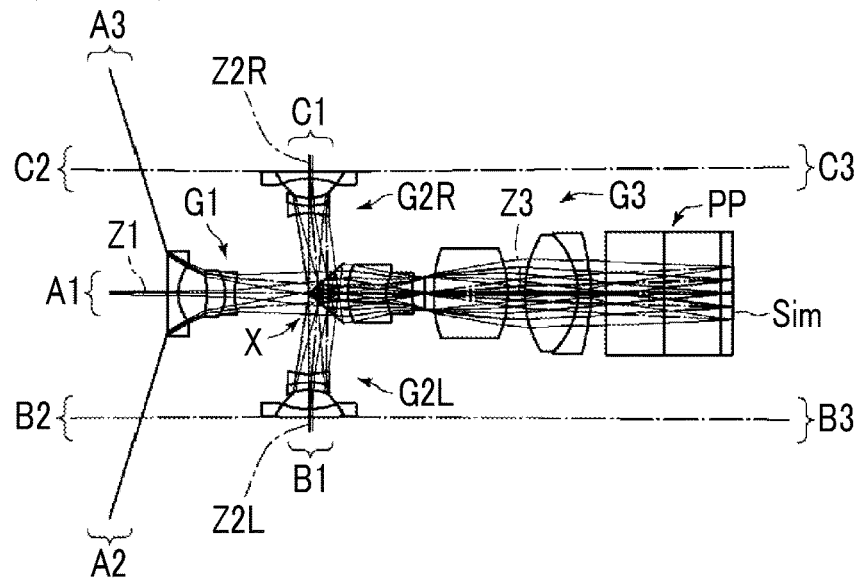
FIG. 5 is an optical path diagram of the endoscope optical system of Example 2.
Figure 5:
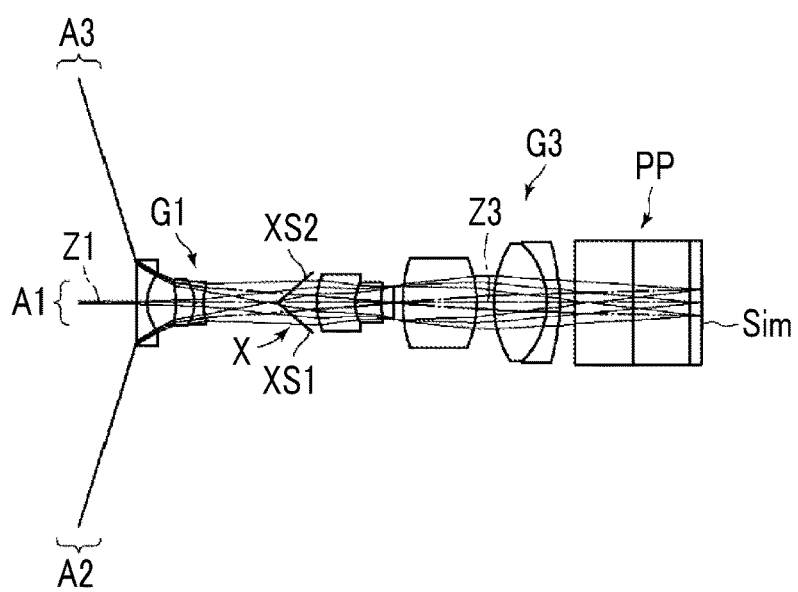
Figure 5:
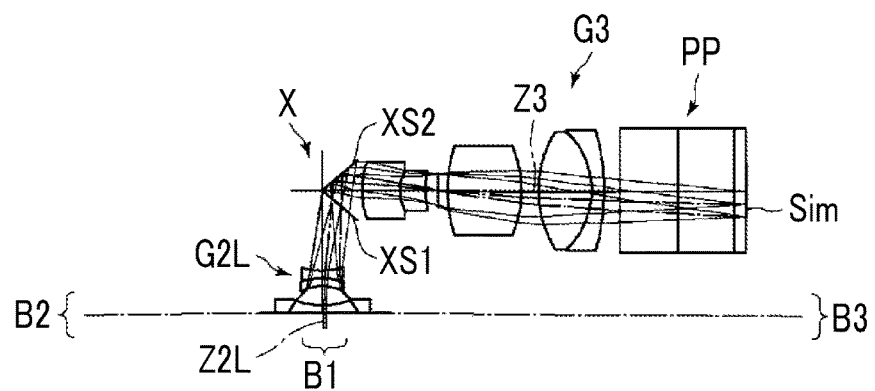
Figure 7:
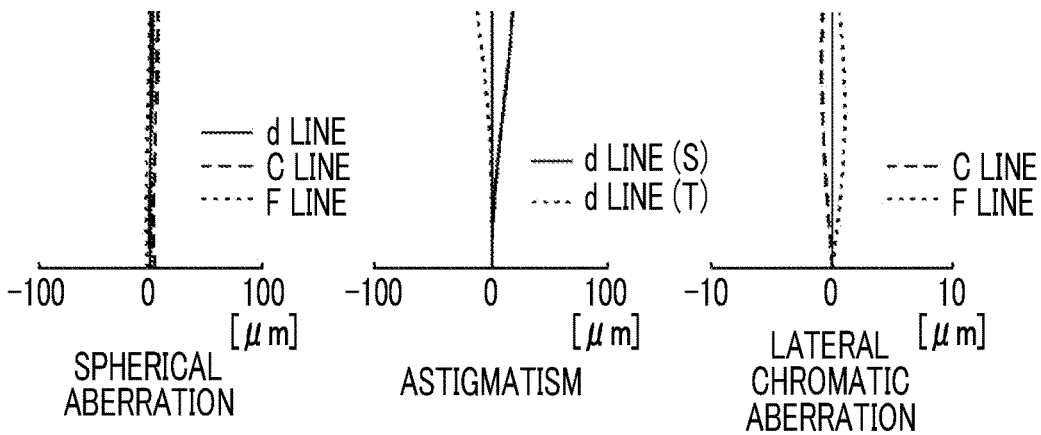
FIG. 7 is a diagram illustrating aberrations of the endoscope optical system of Example 2 of the present invention.
Figure 7:
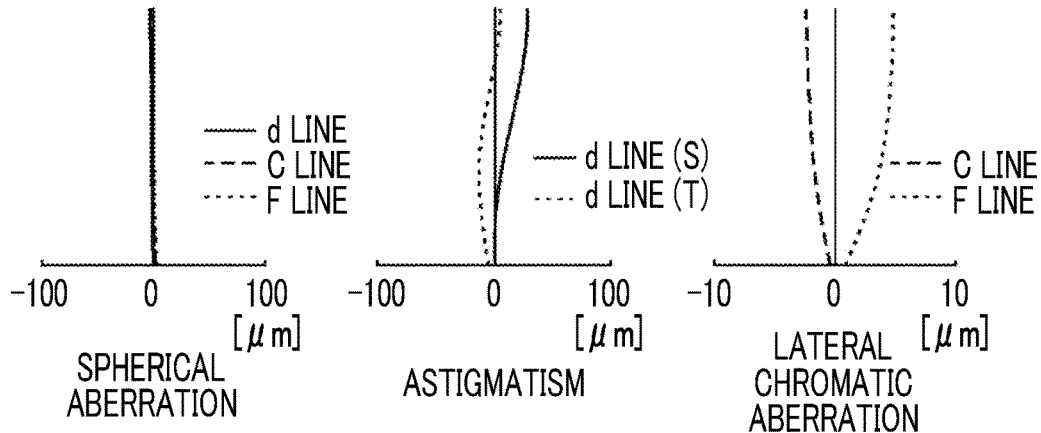
Figure 7:
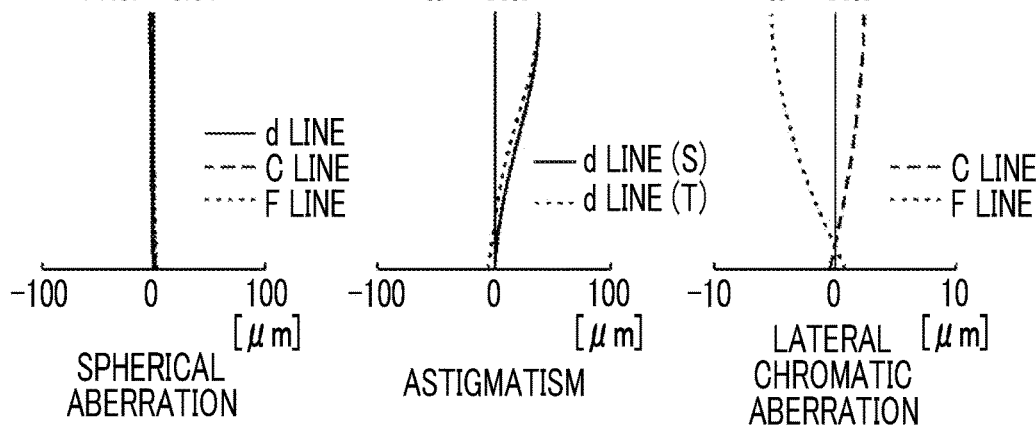

Next, the endoscope optical system of Example 2 will be described. FIG. 4 is a cross-cross-sectional view illustrating the configuration of the endoscope optical system of Example 2. FIG. 5 is an optical path diagram of the endoscope optical system of Example 2. The endoscope optical system of Example 2 has the same number of lenses as the endoscope optical system of Example 1. Further, Table 5 shows basic lens data of the front view optical path of the endoscope optical system of Example 2. Table 6 shows data about specifications of the front view optical path. Table 7 shows basic lens data of the side view optical path. Table 8 shows data about specifications of the side view optical path. FIG. 7 shows a diagram of aberrations.

TABLE 5

Example 2 (First Lens Group + Third Lens Group)
Lens Data (n, ν are based on the d line)

| Surface Number | Radius of Curvature | Surface Distance | n | ν |
|---|---|---|---|---|
| 1 | ∞ | 0.3000 | 1.88300 | 40.81 |
| 2 | 1.2026 | 0.7462 | | |
| 3 | −3.9939 | 0.4969 | 1.94740 | 17.63 |
| 4 | −1.0150 | 0.2336 | 1.88517 | 39.48 |
| 5 | 1.4797 | 2.9913 | | |
| 12 | 1.9403 | 0.9922 | 1.94447 | 25.75 |
| 13 | 1.0305 | 0.6826 | 1.50559 | 59.88 |
| 14 | 2.6369 | 0.3387 | | |
| 15(Stop) | ∞ | 0.2350 | | |
| 16 | 3.5648 | 1.9512 | 1.59531 | 60.93 |
| 17 | −2.8484 | 0.4498 | | |
| 18 | 2.8352 | 1.4000 | 1.49653 | 77.07 |
| 19 | −2.0919 | 0.3395 | 1.82824 | 34.07 |
| 20 | −5.2790 | 0.4000 | | |
| 21 | ∞ | 1.5000 | 1.55920 | 53.92 |
| 22 | ∞ | 1.5000 | 1.55920 | 53.92 |
| 23 | ∞ | 0.3000 | 1.51633 | 64.05 |
| 24 | ∞ | | | |

TABLE 6

Example 2 (First Lens Group +
Third Lens Group) Specification (d line)

| f | 0.34 |
|---|---|
| FNo. | 3.60 |
| 2ω[°] | 145.1 |

TABLE 7

Example 2 (Second Lens Group + Third Lens Group)
Lens Data (n, ν are based on the d line)

| Surface Number | Radius of Curvature | Surface Distance | n | ν |
|---|---|---|---|---|
| 6 | 118.6844 | 0.2000 | 1.88300 | 40.81 |
| 7 | 2.0601 | 0.5000 | | |
| 8 | −1.2163 | 0.2000 | 1.85940 | 42.07 |
| 9 | −2.0000 | 0.2000 | 1.79723 | 47.87 |
| 10 | 1.8336 | 2.0738 | | |
| 11(Half Mirror) | ∞ | 1.0348 | | |
| 12 | 1.9403 | 0.9922 | 1.94447 | 25.75 |
| 13 | 1.0305 | 0.6826 | 1.50559 | 59.88 |
| 14 | 2.6369 | 0.3387 | | |
| 15(Stop) | ∞ | 0.2350 | | |
| 16 | 3.5648 | 1.9512 | 1.59531 | 60.93 |
| 17 | −2.8484 | 0.4498 | | |
| 18 | 2.8352 | 1.4000 | 1.49653 | 77.07 |
| 19 | −2.0919 | 0.3395 | 1.82824 | 34.07 |
| 20 | −5.2790 | 0.4000 | | |
| 21 | ∞ | 1.5000 | 1.55920 | 53.92 |
| 22 | ∞ | 1.5000 | 1.55920 | 53.92 |
| 23 | ∞ | 0.3000 | 1.51633 | 64.05 |
| 24 | ∞ | | | |

TABLE 8

Example 2 (Second Lens Group +
Third Lens Group) Specification (d line)

| f | 1.40 |
|---|---|
| FNo. | 3.61 |
| 2ω[°] | 179.1 |

Table 9 shows values corresponding to Conditional Expressions (1) to (6) of the endoscope optical systems of Examples 1 and 2. It should be noted that, in the above-mentioned examples, the d line is set as the reference wavelength, and the values shown in Table 9 are values at the reference wavelength.

TABLE 9

| Expression Number | Conditional Expression | Example 1 | Example 2 |
|---|---|---|---|
| (1) | f2/F2 | −0.61 | −0.38 |
| (2) | f1/F1 | −1.22 | −1.35 |
| (3) | f3/F1 | 8.81 | 9.66 |
| (4) | νd31 − νd32 | 51.55 | 43.00 |
| (5) | n31 − n32 | −0.36 | −0.33 |
| (6) | νd11 − νd12 | −20.25 | −21.85 |

As can be seen from the above-mentioned data, each endoscope optical system of Examples 1 and 2 satisfies Conditional Expressions (1) to (6), and is capable of separately and simultaneously acquiring two kinds of images of the front view region and the side view region while having favorable optical performance.

Figure 8:
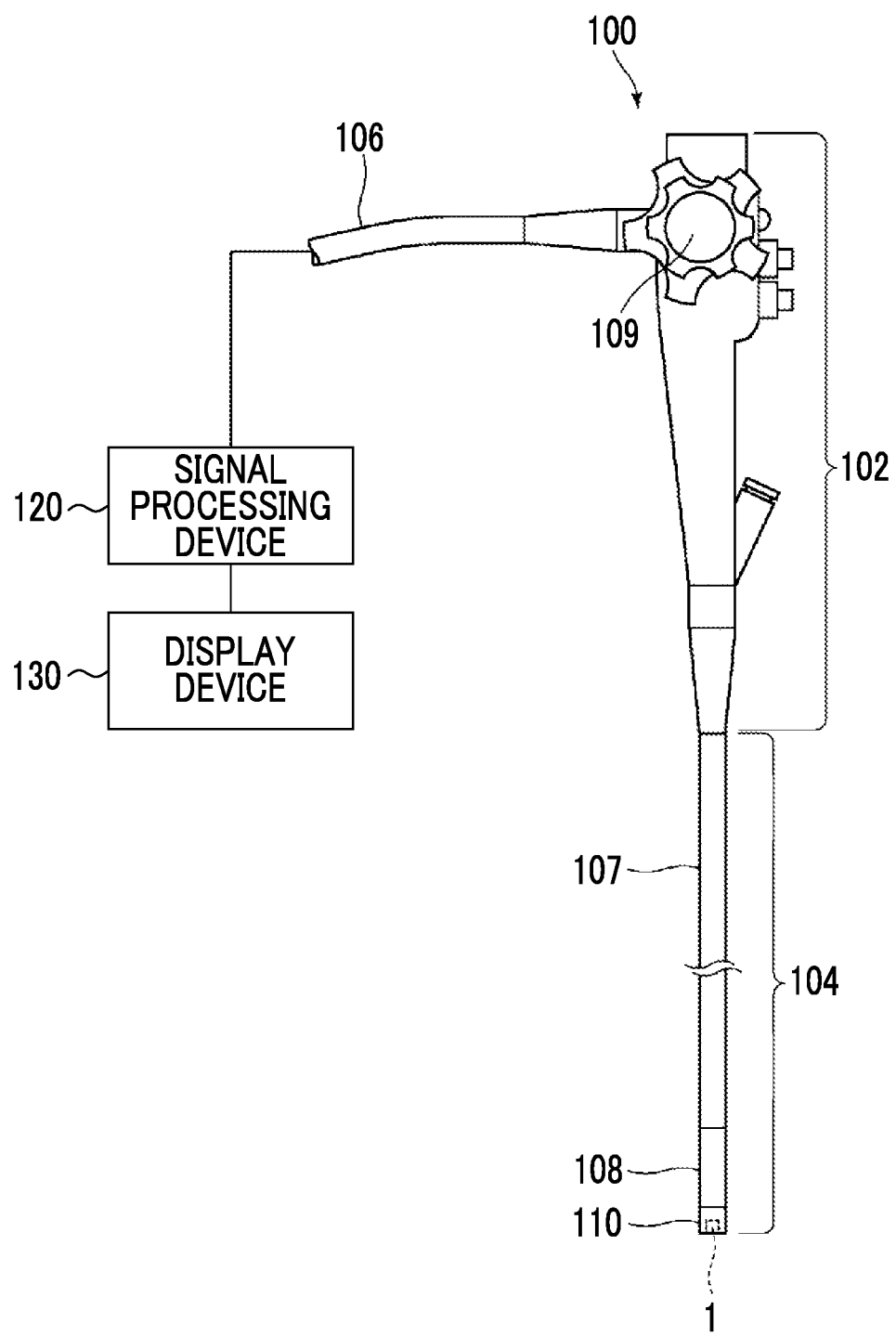
FIG. 8 is a schematic configuration diagram of an endoscopic observation system according to an embodiment of the present invention.
Figure 9:
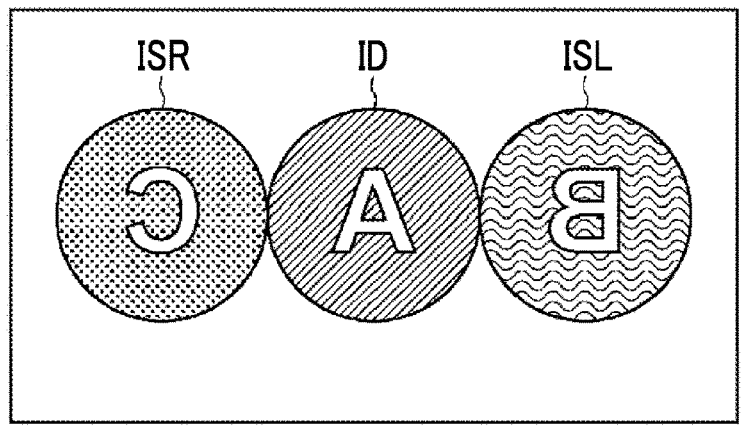
FIG. 9 is a schematic diagram of an image acquired by an endoscope according to an embodiment of the present invention.

Next, an embodiment of an endoscope to which the endoscope optical system of the present invention is applied will be described with reference to FIG. 8. FIG. 8 is a schematic configuration diagram of an endoscopic observation system including the endoscope. FIG. 9 is a schematic diagram of an image acquired by the endoscope. FIGS. 10 to 15 are display examples of endoscopic images in the endoscopic observation system.

The endoscope 100 shown in FIG. 8 mainly includes an operation section 102, an insertion section 104, and a universal cord 106 connected to a connector section (not shown). Most of the insertion section 104 is a flexible portion 107 that bends in an optional direction along the insertion path. A bendable portion 108 is connected to the distal end of the flexible portion 107. A distal end portion 110 is connected to the distal end of the bendable portion 108. The bendable portion 108 is provided to direct the distal end portion 110 in a desired direction, and the bending operation can be performed by rotating the bending operation knob 109 provided in the operation section 102. The endoscope optical system 1 according to the embodiment of the present invention is disposed at the inner distal end of the distal end portion 110. FIG. 8 schematically shows the endoscope optical system 1.

The two kinds of images of the front view region and the side view region acquired by the endoscope optical system 1 are formed on the imaging surface of an imaging element which is not shown. Output signals of the images from the imaging element are processed by the signal processing device 120 and displayed as an endoscopic image on the display device 130.

Here, the two kinds of images of the front view region and the side view region formed on the imaging surface of the imaging element will be described. As shown in FIG. 1, the endoscope 100 provided with the endoscope optical system 1 according to the embodiment of the present invention is able to simultaneously acquire circular images in three directions of a front view region (viewed in the A direction in FIG. 1), a left side view region (viewed in the B direction in FIG. 1), and a right side view region (viewed in the C direction in FIG. 1).

At this time, each image is formed on the imaging surface of the imaging element in the form shown in FIG. 9. In FIG. 9, in order to facilitate understanding of description, an image ID of the front view region is indicated by the letter A schematically shown, an image ISL of the left side view region is indicated by the letter B schematically shown, and an image ISR of the right side view region is indicated by the letter C schematically shown.

In the endoscope optical system 1 according to the embodiment of the present invention, the rays (the rays in the front view region) emitted from the first lens group G1 is transmitted to the third lens group G3 through the synthesizing section X. At this time, the rays emitted from the first lens group G1 pass through the synthesis surface XS1 or the synthesis surface XS2 once, and thus the light amount decreases to ½.

Further, the rays emitted from the second lens group G2L (the rays in the left side view region) are deflected toward the third lens group G3 by the synthesizing section X. However, at this time, the rays emitted from the second lens group G2L are transmitted through the synthesis surface XS1 and are thereafter reflected by the synthesis surface XS2, and thus the light amount decreases to ¼. Furthermore, the rays in the left side view region are reflected by the synthesis surface XS2. Thus, in a case where the image is formed on the imaging surface of the imaging element, as shown in FIG. 9, the image ISL of the left side view region itself is reversed in the horizontal direction and is formed on the right side of the image ID of the front view region.

The rays emitted from the second lens group G2R (the rays in the right side view region) are also deflected toward the third lens group G3 by the synthesizing section X. However, at this time, the rays emitted from the second lens group G2R are transmitted through the synthesis surface XS2 and are thereafter reflected by the synthesis surface XS1, and thus the light amount decreases to ¼. Further, the rays in the right side view region are reflected by the synthesis surface XS1. Thus, in a case where the image is formed on the imaging surface of the imaging element, as shown in FIG. 9, the image ISR of the right side view region itself is horizontally reversed and is formed on the left side of the image ID of the front view region.

The signal processing device 120 performs right-left reverse processing on the image GSL of the image ISL of the left side view region and displays the image GSL on the left side of the image GD of the front view region. Further, the image GSR of the image ISR of the right side view region is horizontally reversed and displayed on the right side of the image GD of the front view region. Furthermore, as described above, the light amount of the image ID of the front view region is differently set to be two times the light amounts of the image ISL of the left side view region and the image ISR of the right side view region. Thus, luminance adjustment processing is performed such that the image GD of the front view region, the image GSL of the left side view region, and the image GSR of the right side view region are equal in luminance.

Figure 10:
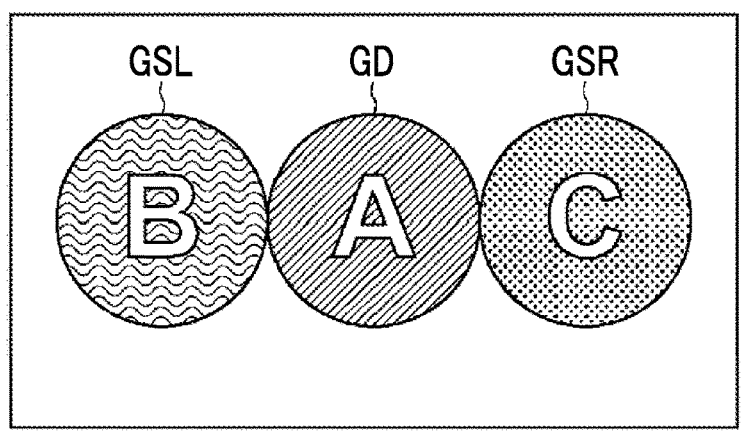
FIG. 10 is a diagram illustrating a display example of an endoscopic image in the endoscopic observation system.

As a result, as shown in FIG. 10, the image GD of the front view region, the image GSL of the left side view region, and the image GSR of the right side view region can be correctly arranged and can be formed as images with uniform luminances.

Figure 11:
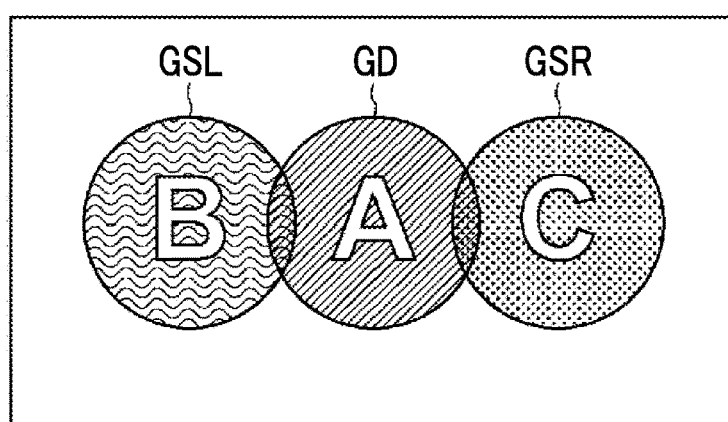
FIG. 11 is a diagram illustrating a display example of an endoscopic image in the endoscopic observation system.

Regarding the images generated by the signal processing device 120, as shown in FIG. 11, in order to naturally connect the front view and the side view, the image GD of the front view region, the image GSL of the left side view region, and the image GSR of the right side view region may be displayed to overlap with each other. The overlap amount may be appropriately adjusted. For example, the overlap is in an area of 5% from the end of each image.

Figure 12:
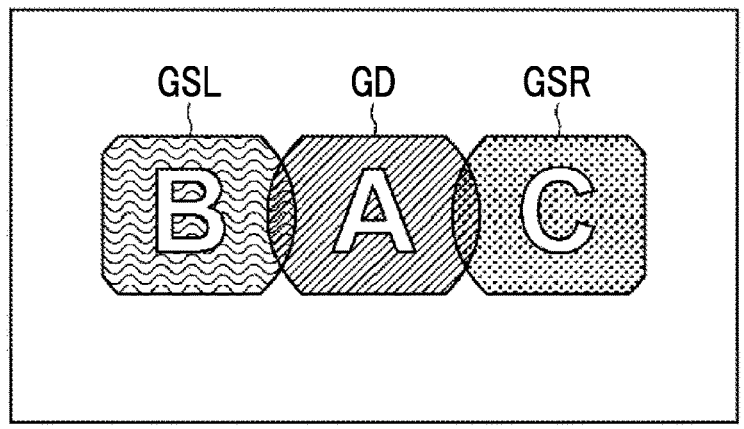
FIG. 12 is a diagram illustrating a display example of an endoscopic image in the endoscopic observation system.

As shown in FIG. 12, the upper, lower, left, and right end portions of the image group, in which the image GD of the front view region, the image GSL of the left side view region, and the image GSR of the right side view region overlap with each other, may be cut off, and the image group may be displayed as a rectangular image.

Figure 13:
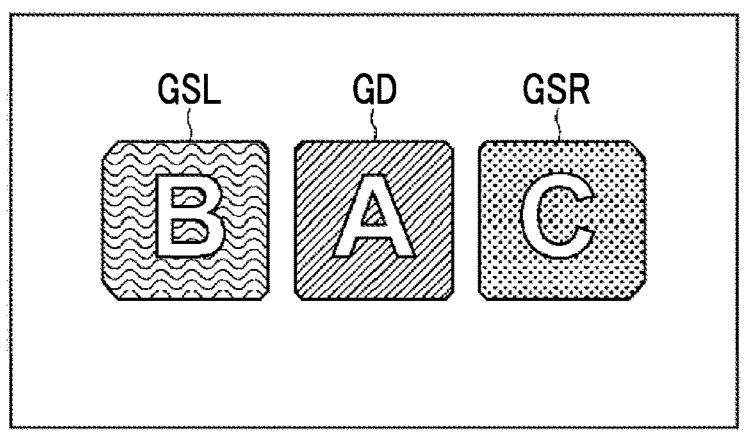
FIG. 13 is a diagram illustrating a display example of an endoscopic image in the endoscopic observation system.

As shown in FIG. 13, the overlapping area of the image group, in which the image GD of the front view region, the image GSL of the left side view region, and the image GSR of the right side view region overlap with each other, may be cut off, and the image group may be displayed.

Figure 14:
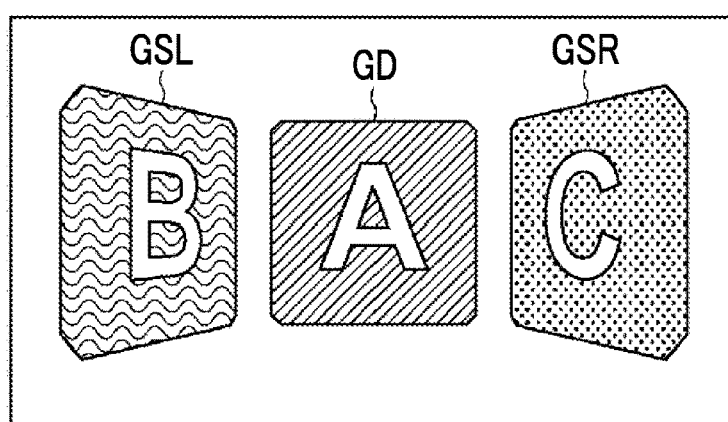
FIG. 14 is a diagram illustrating a display example of an endoscopic image in the endoscopic observation system.

As shown in FIG. 14, the image group, in which the image GD of the front view region, the image GSL of the left side view region, and the image GSR of the right side view region overlap with each other, may be displayed as a perspective corresponding to the positional relationship between the front view region and the side view region such that it is easier to intuitively understand the positional relationship between the side view and the front view.

Since the endoscope of the present embodiment is provided with the endoscope optical system 1, it is possible to separately and simultaneously acquire two kinds of images of the front view region and the side view region.

The present invention has been hitherto described through embodiments and examples, but the present invention is not limited to the above-mentioned embodiments and examples, and may be modified into various forms. For example, the radius of curvature, the surface distance, the refractive index, and the Abbe number of each lens are not limited to the values shown in the above embodiments and may be set as different values.

In the examples of the endoscope optical system of the above embodiment, the two second lens groups are provided. However, the number of the second lens groups is not limited to two, but may be three or more.

Figure 15:
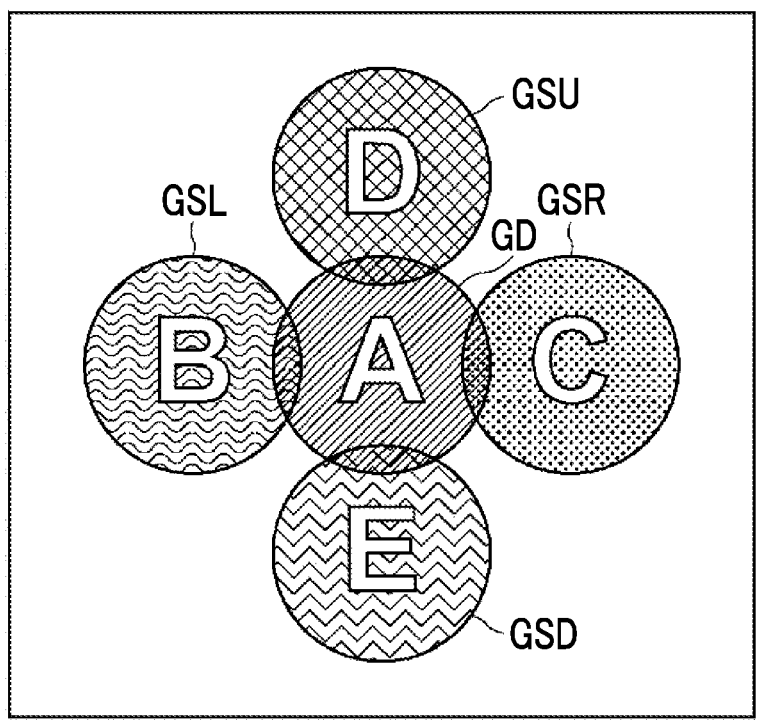
FIG. 15 is a diagram illustrating a display example of an endoscopic image in the endoscopic observation system.

Specifically, four second lens groups directed in four directions of up, down, left, and right from the front view direction as the center may be provided. In this case, as shown in FIG. 15, the image GD of the front view region is centered, and an image GSU of an upper side view region, an image GSD of a lower side view region, the image GSL of the left side view region, and the image GSR of the right side view region are displayed. Thereby, an image with high visibility can be formed.

The synthesis surface in the synthesizing section is not limited to a partially transmissive and partially reflective surface but may be a total reflection surface which is disposed so as to transmit the rays emitted from the first lens group and to totally reflect the rays emitted from the second lens group. With such a configuration, it is possible to suppress a decrease in light amount of the rays in the side view region.

Further, the same lens configuration may be used for all the lens groups of the first lens group and the plurality of second lens groups. With such a configuration, it is possible to simplify the design of the endoscope optical system, and to share components constituting each lens group, such that the increase in cost can be suppressed.

In addition, it is apparent that various variations and modifications may be made without departing from the scope of the present invention.

EXPLANATION OF REFERENCES

1: endoscope optical system
100: endoscope
102: operation section
104: insertion section
106: universal cord
107: flexible portion
108: bendable portion
109: bending operation knob
110: distal end portion
120: signal processing device
130: display device
A1: on-axis rays in front view
A2, A3: rays with maximum angle of view in front view
B1: on-axis rays in left side view
B2, B3: rays with maximum angle of view in left side view
C1: on-axis rays in right side view
C2, C3: rays with maximum angle of view in right side view
CL1a, CL3a: cemented lens
G1: first lens group
G2L, G2R: second lens group
G3: third lens group
L1a to L3e: lens
PP: optical member
Sim: imaging surface
St: aperture stop
X: synthesizing section
XS1, XS2: synthesis surface
Z1: optical axis of first lens group
Z2L, Z2R: optical axis of second lens group
Z3: optical axis of third lens group

What is claimed is:

1. An endoscope optical system capable of both front viewing and side viewing, the endoscope optical system consisting of:
    a first lens group that is used only for front viewing;
    a plurality of second lens groups that each has two or more negative lenses continuously from a position closest to an object side and are used only for side viewing;
    a third lens group that is commonly used in front viewing and side viewing, wherein the third lens group has a third-a cemented lens disposed at a position closest to an image side, wherein the third-a cemented lens consists of a positive lens and a negative lens cemented together, and the positive lens of the third-a cemented lens is disposed closer to the object side relative to the negative lens of the third-a cemented lens; and
    a synthesizing section that has at least one planar synthesis surface, which transmits rays emitted from the first lens group and reflects rays emitted from the second lens groups, so as to synthesize the rays emitted from the first lens group and the rays emitted from the second lens groups and cause the synthesized rays to be incident into the third lens group,
    wherein the rays emitted from the first lens group and the rays emitted from the second lens groups are imaged on a same plane.

2. The endoscope optical system according to claim 1, wherein an entire surface on which the synthesis surface is formed is a partially transmissive and partially reflective surface.

3. The endoscope optical system according to claim 1, wherein the first lens group has a first-a cemented lens in which a positive lens and a negative lens are cemented in order from the object side.

4. The endoscope optical system according to claim 1, wherein assuming that
    a focal length of the first lens group is f1, and
    a composite focal length of the first lens group and the third lens group is F1,
    Conditional Expression (2) is satisfied.

$$-1.5 < f1/F1 < -1.1 \qquad (2)$$

5. The endoscope optical system according to claim 1, wherein assuming that
    a focal length of the third lens group is f3, and
    a composite focal length of the first lens group and the third lens group is F1,
    Conditional Expression (3) is satisfied.

$$5 < f3/F1 < 12 \qquad (3)$$

6. The endoscope optical system according to claim 1, wherein assuming that
    an Abbe number of the positive lens of the third-a cemented lens is vd31, and
    an Abbe number of the negative lens of the third-a cemented lens is vd32,
    Conditional Expression (4) is satisfied.

$$38 < vd31 - vd32 < 58 \qquad (4)$$

7. The endoscope optical system according to claim 1, wherein assuming that
    a refractive index of the positive lens of the third-a cemented lens is n31, and
    a refractive index of the negative lens of the third-a cemented lens is n32,
    Conditional Expression (5) is satisfied.

$$-0.45 < n31 - n32 < -0.28 \qquad (5)$$

8. The endoscope optical system according to claim 3, wherein assuming that
    an Abbe number of the positive lens of the first-a cemented lens is vd11, and
    an Abbe number of the negative lens of the first-a cemented lens is vd12,
    Conditional Expression (6) is satisfied.

$$-40 < vd11 - vd12 < -10 \qquad (6)$$

9. The endoscope optical system according to claim 1, wherein the synthesis surface is inclined with respect to an axis perpendicular to an optical axis of the third lens group.

10. The endoscope optical system according to claim 4, wherein Conditional Expression (2-1) is satisfied.

$$-1.45 < f1/F1 < -1.15 \qquad (2\text{-}1)$$

11. The endoscope optical system according to claim 5, wherein Conditional Expression (3-1) is satisfied.

$$7 < f3/F1 < 10 \qquad (3\text{-}1)$$

12. The endoscope optical system according to claim 6, wherein Conditional Expression (4-1) is satisfied.

$$40 < vd31 - vd32 < 56 \qquad (4\text{-}1)$$

13. The endoscope optical system according to claim 7, wherein Conditional Expression (5-1) is satisfied.

$$-0.43 < n31 - n32 < -0.3 \tag{5-1}$$

14. The endoscope optical system according to claim 8, wherein Conditional Expression (6-1) is satisfied.

$$-38 < vd11 - vd12 < -12 \tag{6-1}$$

15. An endoscope comprising the endoscope optical system according to claim 1.

* * * * *